US008715210B2

(12) United States Patent
Orlando

(10) Patent No.: US 8,715,210 B2
(45) Date of Patent: May 6, 2014

(54) SELF-HEATING MASSAGE STONE

(76) Inventor: Dominic Orlando, Waddell, AZ (US)

(*) Notice: Subject to any disclaimer, the term of this patent is extended or adjusted under 35 U.S.C. 154(b) by 205 days.

(21) Appl. No.: 13/167,614

(22) Filed: Jun. 23, 2011

(65) Prior Publication Data
US 2012/0310120 A1 Dec. 6, 2012

Related U.S. Application Data

(60) Provisional application No. 61/492,086, filed on Jun. 1, 2011.

(51) Int. Cl.
*A61H 1/00* (2006.01)
*H05B 1/00* (2006.01)
*H05B 3/00* (2006.01)

(52) U.S. Cl.
USPC .............. 601/15; 219/201; 219/227; 219/385

(58) Field of Classification Search
USPC ......... 601/15, 18, 19, 46, 64, 78, 80, 94, 118, 601/128, 129, 131, 132, 134, 135, 136, 601/DIG. 1; D24/211, 214; 219/432–433, 219/438, 441, 520, 201, 221, 227, 524, 533
See application file for complete search history.

(56) References Cited

U.S. PATENT DOCUMENTS

| | | | | |
|---|---|---|---|---|
| 1,380,986 | A | * | 6/1921 | Linden .............................. 601/15 |
| 1,534,974 | A | * | 4/1925 | Linden .............................. 601/15 |
| 2,744,995 | A | * | 5/1956 | Jepson ........................... 219/441 |
| 3,822,781 | A | * | 7/1974 | Braginetz ....................... 206/776 |
| 5,261,352 | A | | 11/1993 | Stammelman |
| 5,274,215 | A | * | 12/1993 | Jackson ......................... 219/439 |
| D345,801 | S | | 4/1994 | Bosch |
| 5,406,054 | A | | 4/1995 | Chirdon |

(Continued)

FOREIGN PATENT DOCUMENTS

| | | |
|---|---|---|
| DE | 20212601 | 2/2003 |
| DE | 102008014002 | 9/2009 |

(Continued)

OTHER PUBLICATIONS

Website accessed on Nov. 22, 2010 entitled NU Warn Stone Portable Heater (EWG001) source: http://www.meritline.com/portable-heater-warm-stone-pink-nu-ewg001---p-57800.aspx.

(Continued)

*Primary Examiner* — Justine Yu
*Assistant Examiner* — Christopher Miller
(74) *Attorney, Agent, or Firm* — Greenblum & Bernstein, P.L.C.

(57) ABSTRACT

A pocket-size self-heating massage stone includes a first receptacle having a rim portion, an interior recess and being made of ceramic slip, porcelain or stoneware slip and a second receptacle having a rim portion, an interior recess and being made of ceramic slip, porcelain or stoneware slip. A heating element is arranged in the interior recess of the second receptacle and being positioned in direct contact to transmit heat directly to a surface of the second receptacle such that the heating element only directly heats the second receptacle and does not directly heat the first receptacle. A rechargeable battery is disposed within the massage stone. The first and second receptacles are connected to one another via only the rim portions and the interior recesses of the first and second receptacles are free of connectors which connect together the first and second receptacles.

1 Claim, 5 Drawing Sheets

(56) References Cited

U.S. PATENT DOCUMENTS

| | | | |
|---|---|---|---|
| 5,653,345 A * | 8/1997 | Knoss et al. | 206/521.6 |
| 5,683,007 A * | 11/1997 | Scholfield | 220/755 |
| 6,001,070 A * | 12/1999 | Gebhard | 601/15 |
| 6,028,293 A * | 2/2000 | Nagle et al. | 219/432 |
| 6,070,718 A * | 6/2000 | Drabwell | 206/216 |
| 6,144,016 A * | 11/2000 | Garvin | 219/387 |
| 6,320,161 B1 * | 11/2001 | Hansen, Jr. | 219/211 |
| 6,674,052 B1 * | 1/2004 | Luo | 219/520 |
| 6,864,462 B2 * | 3/2005 | Sanoner et al. | 219/387 |
| 6,866,776 B2 * | 3/2005 | Leason et al. | 210/201 |
| 7,276,676 B1 * | 10/2007 | Thompson | 219/439 |
| D560,810 S | 1/2008 | Hennessy | |
| D571,926 S | 6/2008 | Wu | |
| D586,469 S | 2/2009 | Henry | |
| D626,656 S | 11/2010 | Jarry | |
| 8,167,166 B2 * | 5/2012 | Kidd et al. | 220/835 |
| 8,278,606 B2 * | 10/2012 | Toya et al. | 219/533 |
| 2002/0026133 A1 * | 2/2002 | Augustine et al. | 602/2 |
| 2006/0287696 A1 * | 12/2006 | Wright et al. | 607/88 |
| 2008/0053979 A1 * | 3/2008 | Toya et al. | 219/201 |
| 2010/0286577 A1 * | 11/2010 | Tsai | 601/112 |
| 2011/0000116 A1 * | 1/2011 | Rain | 40/724 |
| 2011/0103776 A1 * | 5/2011 | Jorgensen | 392/386 |
| 2011/0144546 A1 * | 6/2011 | Crothers et al. | 601/15 |
| 2013/0085422 A1 * | 4/2013 | Gillespie et al. | 601/17 |

FOREIGN PATENT DOCUMENTS

| | | |
|---|---|---|
| FR | 2935609 | 3/2010 |
| GB | 2446426 | 8/2008 |
| KR | 10-2005-0113494 B1 * | 2/2007 |
| WO | WO2010/112915 | 10/2010 |

OTHER PUBLICATIONS

Website accessed on Nov. 22, 2010 entitled Rechargeable Body Warmer Source: http://www.taiwantrade.com.tw/EP/Samples.do?Method=showSampleDetail&catalogId=468643&epDomainName=justpower.

Link accessed on Nov. 22, 2010 entitled Hand Warmers: Small packets of warmth work through a simple exothermic reaction by Linda Wang; Chemical and Engineering news, Jan. 25, 2010, vol. 88, No. 4, p. 36, Source: http://pubs.acs.org/cen/science/88/8804sci3.html.

* cited by examiner

SELF-HEATING MASSAGE STONE

RELATED APPLICATIONS

This invention claims the priority benefit of U.S. Provisional Patent Application No. 61/492,086 filed on 1 Jun. 2011, which application is incorporated by reference herein. The present application is further related to Design application 29/384,207 filed Jan. 27, 2011 and is hereby incorporated herewith.

FIELD OF THE INVENTION

This invention relates to massage devices, and more specifically, to a self heating massage stone.

BACKGROUND OF THE INVENTION

Massage therapy may involve the manual manipulation of soft body tissues to enhance the general health and well-being of a patient or a user. The manual manipulation may involve applying a pressure, a tension, a vibration to the soft body tissues with the help of various aids such as massage stones, massage lotions, essential oils, and the like.

Massage stones are used in stone massage therapy by heating the massage stones before applying to the soft body tissues. Massage stones are usually made of basalt, which is rich in iron and has the ability to retain heat.

Conventionally, massage stones are immersed in water that is then heated in an electric heating device until the massage stones attain a certain temperature range. After heating the hot massage stones are removed and applied to the soft body tissues. The therapist also massages the client's soft tissues with the warm stones, which may relieve tension, loosen adhesions, increase circulation, etc.

However, there are several issues with massage stones. First, the therapist conducting the stone massage therapy has to ensure that the massage stones are a suitable temperature for use during therapy. Many times the stones are too hot, or not hot enough. Second, current massage stones tend to lose heat attained during the massage. Thus, the therapist/client contact may be interrupted every time the therapist must stop to get new heated stones because the stones in use have lost their heat.

Therefore, it would be desirable to provide a device and method that overcomes the above problems.

SUMMARY

In accordance with one embodiment of the present invention, a heated massage stone is disclosed. The heated massage stone has a first receptacle having a first interior recess and a second receptacle having a second interior recess. A heating element is positioned in one of the first interior recess or the second interior recess. An attachment device is used to secure the first receptacle to the second receptacle In accordance with one embodiment of the present invention, a heated massage stone is disclosed. The heated massage stone has a first receptacle having a first interior recess and a second receptacle having a second interior recess. A heating element is positioned in one of the first interior recess or the second interior recess. A rechargeable battery is attached to the heating element. A plurality of magnets is attached to a rim of the first receptacle and to a rim of the second receptacle to secure the first receptacle to the second receptacle.

In accordance with one embodiment of the present invention, a heated massage stone is disclosed. The heated massage stone has a first receptacle having a first interior recess and a second receptacle having a second interior recess. A heating element is positioned in one of the first interior recess or the second interior recess. An insulation layer is attached to the heating element. A rechargeable battery is attached to the heating element. A plurality of magnets are attached to a rim of the first receptacle and to a rim of the second receptacle to secure the first receptacle to the second receptacle so that the first and second interior recesses form a cavity to retain the heating element The features, functions, and advantages can be achieved independently in various embodiments of the disclosure or may be combined in yet other embodiments.

The invention also provides for a pocket-size self-heating massage stone, including a first receptacle having a rim portion, an interior recess and being made of ceramic slip, porcelain or stoneware slip and a second receptacle having a rim portion, an interior recess and being made of ceramic slip, porcelain or stoneware slip. A heating element is arranged in the interior recess of the second receptacle and being positioned in direct contact to transmit heat directly to a surface of the second receptacle such that the heating element is not embedded in a wall of the second receptacle and only directly heats the second receptacle and does not directly heat the first receptacle. A rechargeable battery is disposed within the massage stone. The first and second receptacles are connected to one another via only the rim portions and the interior recesses of the first and second receptacles are free of connectors which connect together the first and second receptacles.

The invention also provides for a pocket-size self-heating massage stone, including a first semi-oval shaped receptacle having an interior recess and being made of ceramic slip, porcelain or stoneware slip and a second semi-oval shaped receptacle having an interior recess and being made of ceramic slip, porcelain or stoneware slip. A heating element is arranged in the interior recess of the second receptacle and being positioned in direct contact to transmit heat directly to an inner surface of the second receptacle, wherein the heating element is not embedded in a wall of the second receptacle. A rechargeable battery is disposed within the massage stone. An insulating cover is structured and arranged to prevent heat from dissipating toward the first receptacle when the heating element directly heats the second receptacle. Plural connectors are structured and arranged to connect a rim portion of the first receptacle to a rim portion of the second receptacle. The plural connectors are arranged on the rim portions of the first and second receptacles and the interior recesses of the first and second receptacles are free of connectors which connect together the first and second receptacles.

The invention also provides for a pocket-size self-heating massage stone, including a first semi-oval shaped and non-directly heated receptacle comprising an interior recess and exterior glazing and being made of ceramic slip, porcelain or stoneware slip and a second semi-oval shaped and directly heated receptacle having an interior recess and being made of ceramic slip, porcelain or stoneware slip having an exterior glazing. A heating element is arranged in the interior recess of the second receptacle and being positioned in direct contact to transmit heat directly to a surface of the second receptacle so as to directly heat the second receptacle, wherein the heating element is not embedded in a wall of the second receptacle. A rechargeable battery is disposed within the massage stone. An insulating cover is structured and arranged to prevent heat from dissipating toward the first receptacle. A plurality of connectors are structured and arranged to connect a rim portion of the first receptacle to a rim portion of the second receptacle. All of the plurality of connectors are located on the rim portions and include magnets and the interior recesses of the first and second receptacles are free of connectors which connect together the first and second receptacles.

BRIEF DESCRIPTION OF THE DRAWINGS

Embodiments of the disclosure will become more fully understood from the detailed description and the accompanying drawings, wherein.

DETAILED DESCRIPTION OF THE INVENTION

Figure 1:
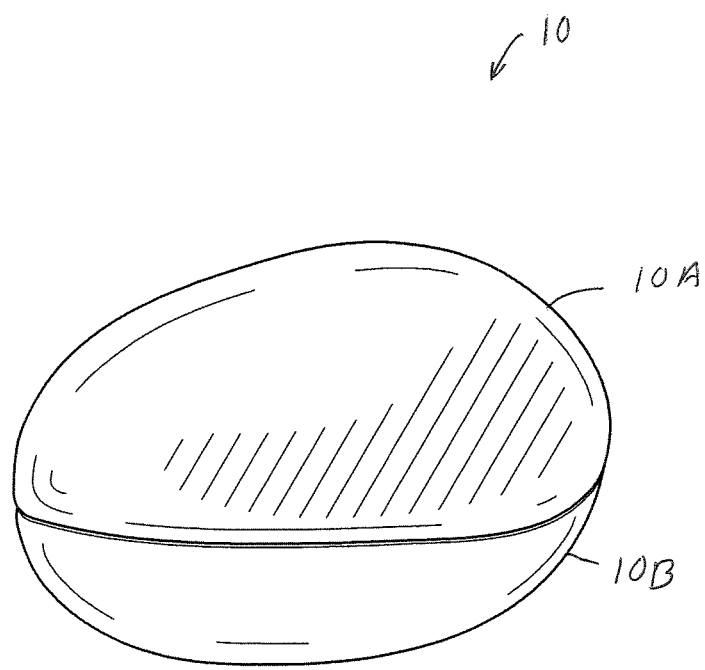
FIG. 1 is a perspective view of the self heating massage stone.
Figure 2A:
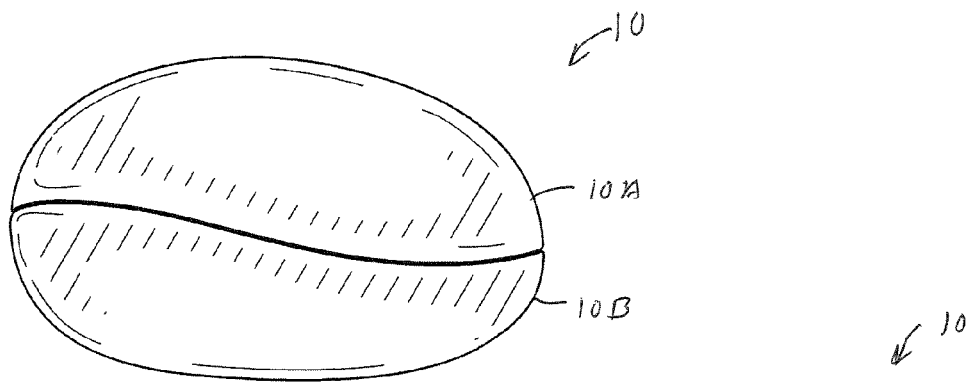
FIG. 2a is left side view of the self heating massage stone.
Figure 2B:
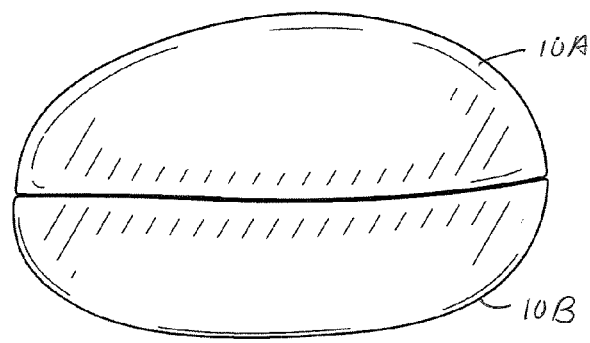
FIG. 2b is a right side view of the self heating massage stone.
Figure 3A:
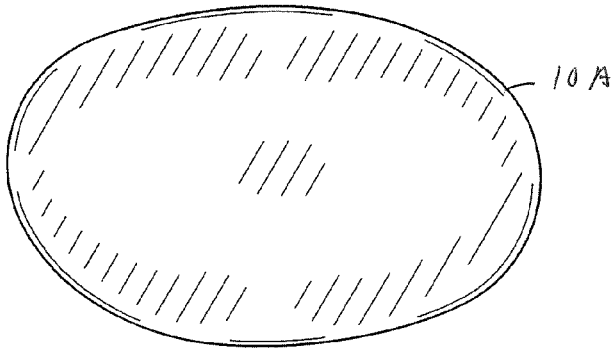
FIG. 3a is top view of the self heating massage stone.
Figure 3B:
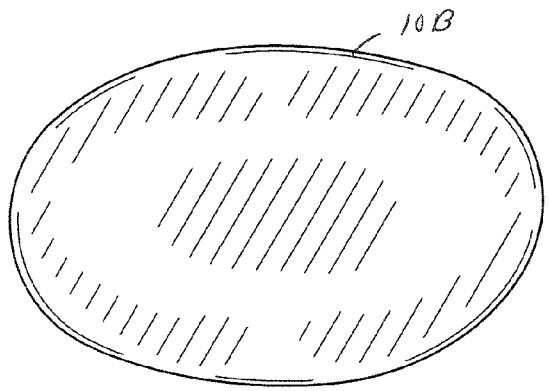
FIG. 3b is a bottom view of the self heating massage stone.
Figure 4A:
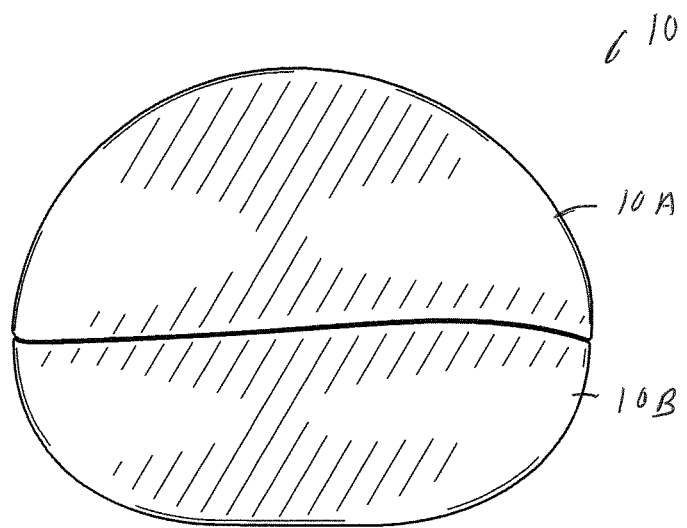
FIG. 4a is front view of the self heating massage stone.
Figure 4B:
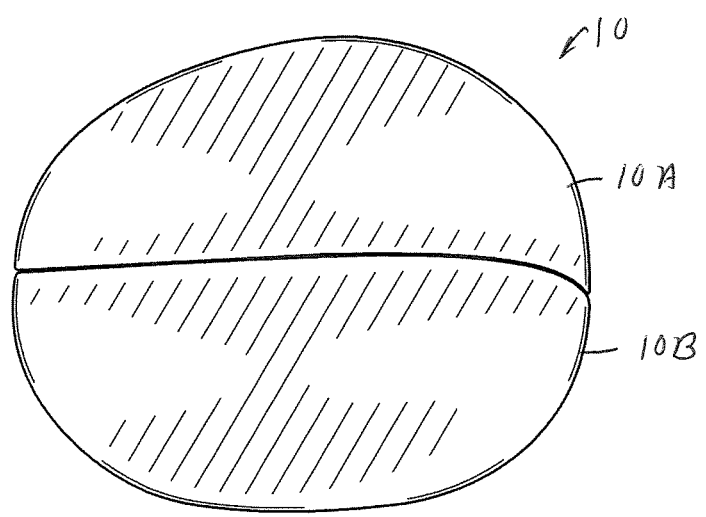
FIG. 4b is a rear view of the self heating massage stone.
Figure 5:
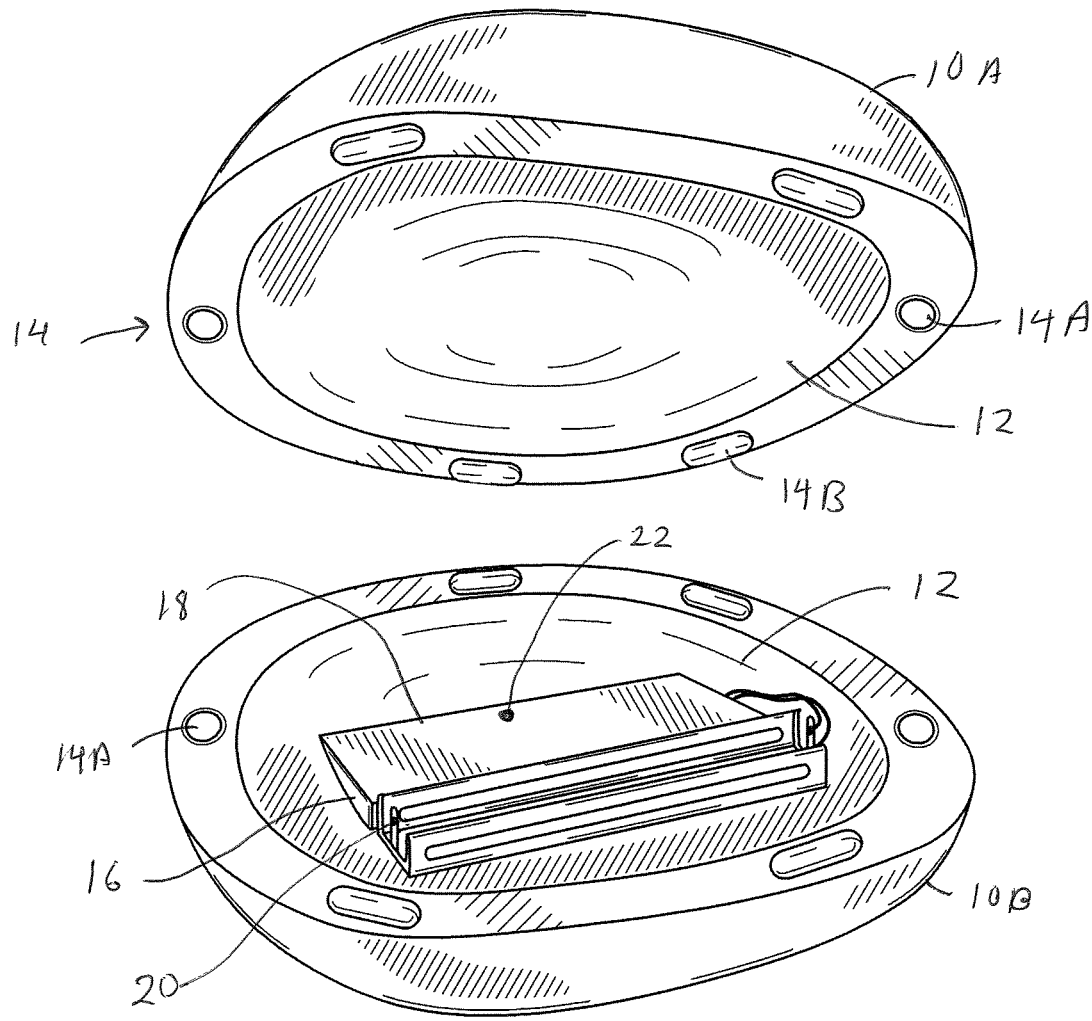
FIG. 5 is an exploded view the self heating massage stone.
Figure 6A:
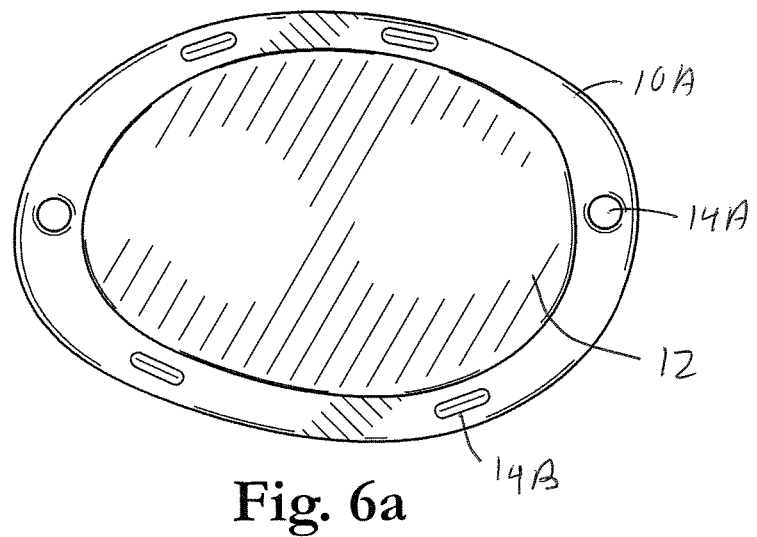
FIG. 6a is top inside view of the self heating massage stone.
Figure 6B:
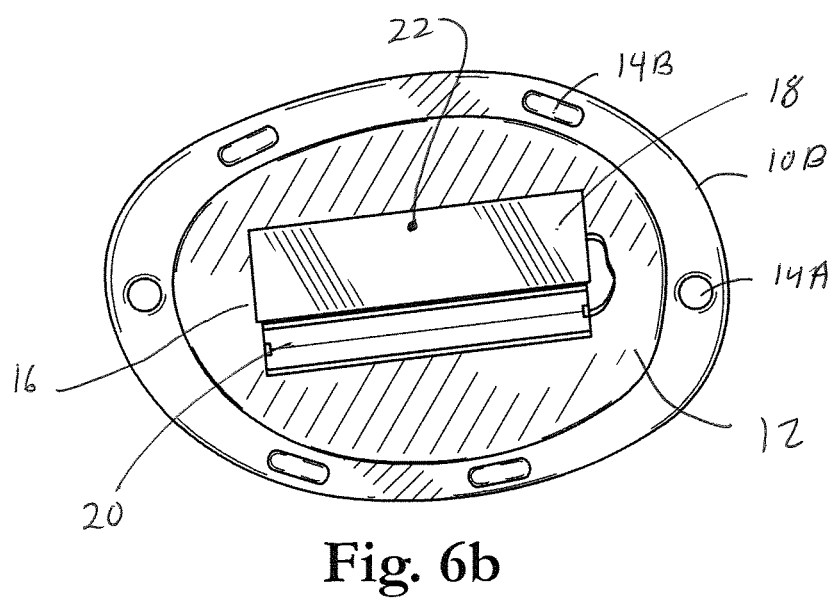
FIG. 6b is a bottom inside view of the self heating massage stone.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention generally provides a self-heating massage stone. Presently, stones used in a hot stone massage do not stay hot long enough. Embodiments of the present invention may allow one to give a stone massage for an entire treatment without having to switch out new stones.

As depicted in the Figures, an embodiment of a massage stone 10 is shown. In accordance with one embodiment, the massage stone 10 may be formed out of ceramic. A ceramic material may be used as certain types of ceramics have the ability to readily dissipate heat. Further, the coloration and texture is intrinsic to the ceramic materials and so painting or other kinds of surface protection is not necessary in recurring maintenance.

In accordance with one embodiment, the massage stone 10 may be formed as a two piece 10A and 10B massage stone. As may be seen in the Figures, each piece 10A and 10B may be formed semi-oval in shape to look like current massage stones. Each piece 10A and 10B may be formed with a semi-hollow interior 12.

In accordance with one embodiment, the massage stone 10 may be formed by using a two piece mold in the shape of a massage stone and a ceramic slip, or porcelain, or stoneware slip is poured in the mold. The mold may be formed by obtaining a stone and making a plaster mold of the stone using a double sided mold.

Once set or dried, the bisque stone shapes may be taken out of the mold and set to dry. Once dried the bisque stone shapes may go into a kiln where the bisque stone shapes may be low fired or bisque fired. The bisque stone shapes may then be taken out and cooled, then glazed with a black shiny glaze. The bisque stone shapes may then be fired again in the kiln forming the two pieces 10A and 10B of the massage stone 10.

Once the two pieces 10A and 10B are taken out, connectors 14 may be placed around an interior rim 16 of each of the two pieces 10A and 10B. The connectors 14 may be used to secure the two pieces 10A and 10B together to form the massage stone 10 as a single unit which may resemble a basalt stone.

In accordance with one embodiment, a plurality of magnets 14A may be placed in the interior rim 16 of each of the two pieces 10A and 10B. The magnets 14A may be positioned so that corresponding magnets 14A may be aligned on each of the two pieces 10A and 10B when the two pieces 10A and 10B are attached. Also, the corresponding magnets 14A should be of opposite polarity so that the two pieces 10A and 10B attach to one another. While the massage stone 10 may be held together by magnets 14A, other methods may be used without departing from the spirit and scope of the present invention. Alternative methods may be used such as using keys 14B that may be molded into the two pieces 10A and 10B. One side has a male key and the other side has the female key into which the male key fits.

In an embodiment, a heating element 16 may be positioned in the interior of one of the two pieces 10A or 10B. The heating element 16 may be used to warm the hollowed out ceramic massage stone 10 and keeps it warm. The heating element 16 may transmit heat to the surface of the piece 10A or 10B in which the heating element 16 is positioned. The heating element 16 may have an insulated cover 18. The insulated cover 18 may prevent heat from dissipating outward toward the other piece 10A or 10B in which the heating element 16 is not positioned.

The heating element 16 may be powered by a rechargeable battery 20. The rechargeable battery 20 may be a lithium ion battery or the like.

The heating element 16 may be adjustable to control the temperature of the massage stone 10. Further, the heating element 16 may keep the massage stone 10 continuously warm as the rechargeable battery 20 is able to power the heating element and keep the ceramic stone warm for the entire treatment. In contrast, conventional stones only stay hot for five minutes and then the therapist has to leave the clients body and get new stones. A process that has to constantly be repeated throughout the treatment.

To use an embodiment, activate the heating element 16. This may be done by turning on a switch 22 to the heating element. The switch 22 may be located external on the massage stone 10. Alternatively, one may have to open the two halves 10A and 10B of the massage stone 10 and turn on a switch 22 located on/near the heating element 16. Once activated, oil may be placed on the massage stone 10 and give a massage with them to a person. People can put them in their pockets as hand warmers as well.

Other embodiments may have different shapes for the massage stone 10, or different sources of heat on the inside.

It should be understood, of course, that the foregoing relates to exemplary embodiments of the invention and that modifications may be made without departing from the spirit and scope of the invention as set forth in the following claims.

I claim:

1. A pocket-size self-heating massage stone, consisting of:
a first semi-oval shaped and non-directly heated receptacle comprising an interior recess and exterior glazing and being made of ceramic slip, porcelain or stoneware slip;
a second semi-oval shaped and directly heated receptacle having an interior recess and being made of ceramic slip, porcelain or stoneware slip having an exterior glazing;
a heating element arranged in the interior recess of the second receptacle and being positioned in direct contact to transmit heat directly to a surface of the second receptacle so as to directly heat the second receptacle, wherein the heating element is not embedded in a wall of the second receptacle;
a rechargeable battery disposed within the massage stone;
an insulating cover structured and arranged to prevent heat from dissipating toward the first receptacle; and
a plurality of connectors structured and arranged to connect a rim portion of the first receptacle to a rim portion of the second receptacle,
wherein all of the plurality of connectors are located on the rim portions and include magnets and the interior recesses of the first and second receptacles are free of connectors which connect together the first and second receptacles.

* * * * *